(12) United States Patent
Hahnl et al.

(10) Patent No.: US 11,071,192 B2
(45) Date of Patent: Jul. 20, 2021

(54) FLAT FLEXIBLE SUPPORT PIECE FOR A DIELECTRICALLY IMPEDED PLASMA TREATMENT

(71) Applicant: Cinogy GmbH, Duderstadt (DE)

(72) Inventors: Mirko Hahnl, Berlingerode (DE);
Karl-Otto Storck, Duderstadt (DE);
Leonhard Trutwig, Duderstadt (DE);
Dirk Wandke, Heilbad Heiligenstadt (DE)

(73) Assignee: Cinogy GmbH, Duderstadt (DE)

( * ) Notice: Subject to any disclaimer, the term of this patent is extended or adjusted under 35 U.S.C. 154(b) by 0 days.

(21) Appl. No.: 16/475,399

(22) PCT Filed: Dec. 20, 2017

(86) PCT No.: PCT/DE2017/101097
§ 371 (c)(1),
(2) Date: Jul. 2, 2019

(87) PCT Pub. No.: WO2018/127257
PCT Pub. Date: Jul. 12, 2018

(65) Prior Publication Data
US 2019/0327823 A1    Oct. 24, 2019

(30) Foreign Application Priority Data
Jan. 5, 2017 (DE) .................. 10 2017 100 161.1

(51) Int. Cl.
*H05H 1/24* (2006.01)
*A61L 2/14* (2006.01)
(Continued)

(52) U.S. Cl.
CPC ............. *H05H 1/2406* (2013.01); *A61L 2/14* (2013.01); *A61N 1/0468* (2013.01);
(Continued)

(58) Field of Classification Search
None
See application file for complete search history.

(56) References Cited

U.S. PATENT DOCUMENTS

| 2005/0110145 A1* | 5/2005 | Elers ............... H01L 21/288 257/758 |
| 2012/0271225 A1* | 10/2012 | Stieber ............ A61B 18/042 604/26 |

(Continued)

FOREIGN PATENT DOCUMENTS

| DE | 698 02 094 T2 | 6/2002 |
| DE | 101 36 403 A1 | 2/2003 |

(Continued)

*Primary Examiner* — Kishor Mayekar
(74) *Attorney, Agent, or Firm* — W & C IP

(57) ABSTRACT

In the case of a flat flexible support piece comprising an electrode arrangement, to which a high voltage can be supplied, for a dielectrically impeded plasma treatment of a surface to be treated, wherein the electrode arrangement has at least one flat electrode (3) and a dielectric layer (2) which has a support face for the surface to be treated and which is composed of flat flexible material and which electrically shields the at least one electrode (3) from the surface to be treated such that only a dielectrically impeded current flow between the at least one electrode (3) and the surface to be treated is possible when a plasma field is produced by the bias on the electrode (3) in a gas space between the electrode arrangement and the surface to be treated, simplified handling and increased safety are achieved in that the support piece has a high-voltage stage (14) for generating a high voltage, the output of said high-voltage stage being connected to the at least one electrode (3) by a connecting piece (17, 17') on the support piece.

10 Claims, 7 Drawing Sheets

(51) Int. Cl.
*A61N 1/04* (2006.01)
*A61N 1/32* (2006.01)
*A61N 1/44* (2006.01)

(52) U.S. Cl.
CPC .......... *A61N 1/0476* (2013.01); *A61N 1/326* (2013.01); *A61N 1/44* (2013.01); *H05H 2245/122* (2013.01); *H05H 2245/125* (2013.01)

(56) References Cited

U.S. PATENT DOCUMENTS

2013/0345620 A1* 12/2013 Zemel .................. A61B 18/042
  604/24
2015/0157870 A1    6/2015 Khalghatgi et al.
2016/0331989 A1   11/2016 Cho
2017/0231680 A1*   8/2017 Mahrenholz ............. A61N 1/44
  606/34

FOREIGN PATENT DOCUMENTS

| DE | 20 2008 008 736 U1 | 12/2009 |
| DE | 10 2008 030 913 A1 | 1/2010 |
| DE | 10 2009 060 627 B4 | 6/2011 |
| DE | 10 2011 100 751 A1 | 11/2012 |
| DE | 10 2011 105 713 A1 | 12/2012 |
| DE | 10 2014 013 716 A1 | 3/2016 |
| DE | 10 2015 101 391 A1 | 8/2016 |
| EP | 2 723 447 B1 | 4/2014 |
| EP | 2 946 641 B1 | 11/2015 |
| EP | 3 051 926 A1 | 8/2016 |
| WO | WO 2016/055654 * | 4/2016 |
| WO | 2016/186501 A2 | 5/2016 |

* cited by examiner

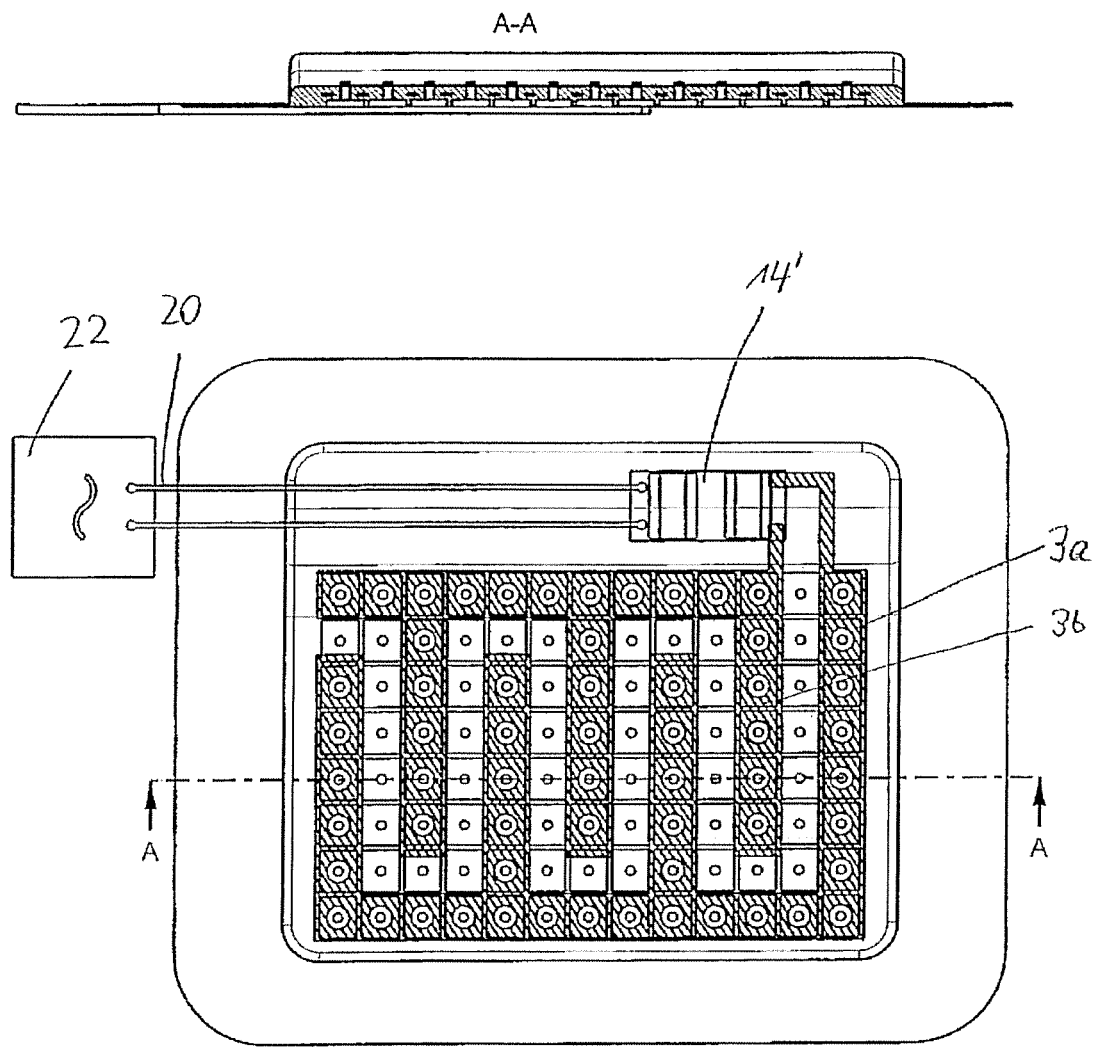

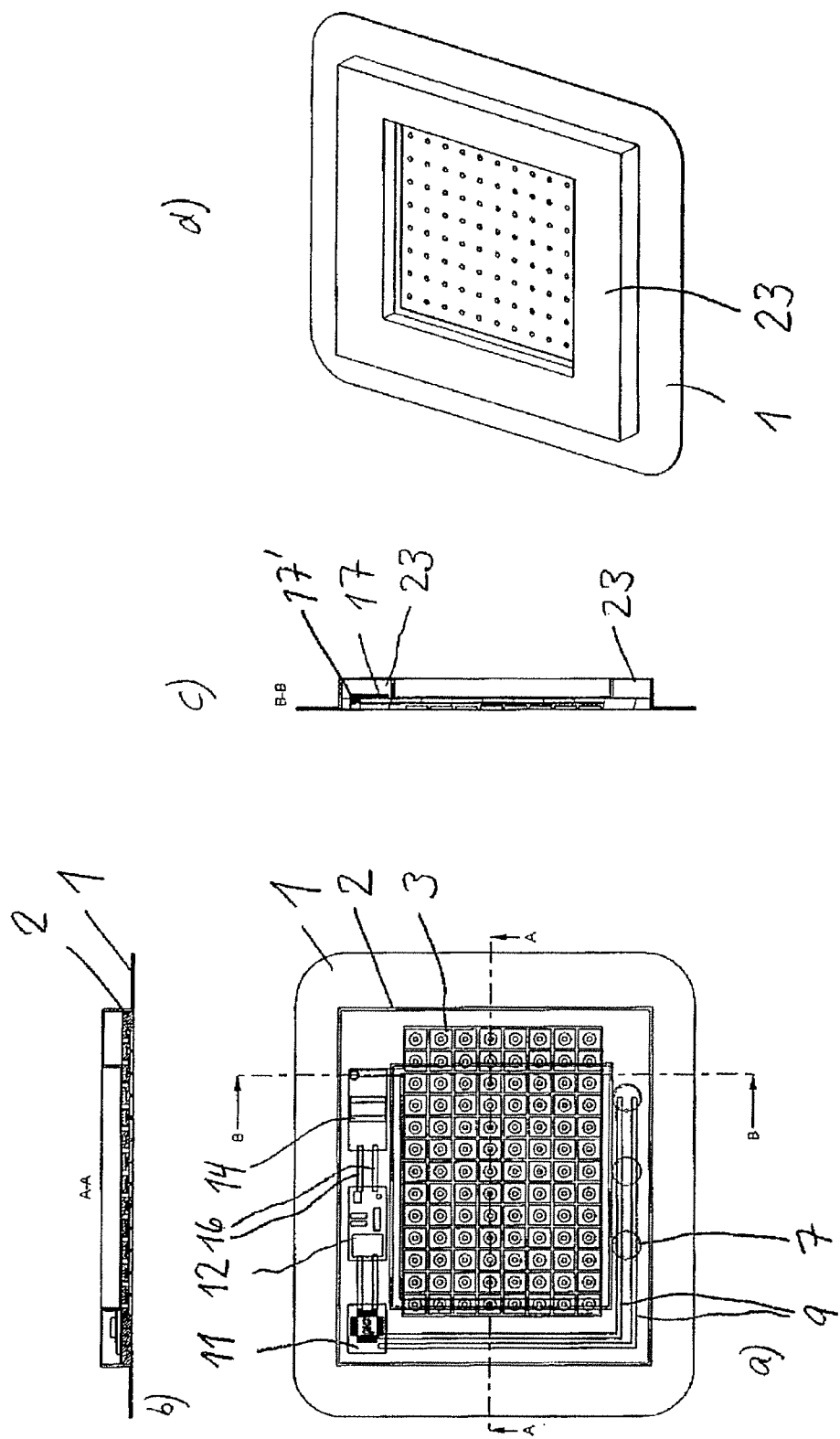

FLAT FLEXIBLE SUPPORT PIECE FOR A DIELECTRICALLY IMPEDED PLASMA TREATMENT

FIELD OF THE INVENTION

The invention relates to a planar flexible application piece having an electrode arrangement, which can be supplied with a high voltage, for a dielectric barrier plasma treatment of a surface to be treated, the electrode arrangement comprising at least one planar electrode and a dielectric layer of a planar flexible material having a bearing face for the surface to be treated, said dielectric layer electrically shielding the at least one electrode from the surface to be treated in such a way that only a dielectric barrier current can flow between the at least one electrode and the surface to be treated when a plasma field is formed in a gas space between the electrode arrangement and the surface to be treated by the high voltage of the electrode.

BACKGROUND

The treatment of surfaces, which also includes human skin, with a dielectric barrier plasma field is known. For example, DE 10 2009 060 627 B4 discloses a planar flexible application piece having the above features. The planar and flexible electrode, which is preferably fully enclosed by the dielectric in this case, is supplied in a suitable way via a high-voltage cable with a high voltage which is required for the formation of the dielectric barrier plasma field. The contacting of the electrode may be carried out at an electrode terminal which is fitted in a housing and protrudes from the dielectric layer. In an arrangement disclosed by EP 2 723 447 B1, the contacting of the electrode is carried out by means of a cutting contact which is pushed through the dielectric layer so as to contact the electrode through the dielectric. This cutting contact is arranged in a contact housing by which contacting of an operator with the high voltage is reliably prevented.

EP 2 946 641 B1 discloses, for an electrode arrangement especially described with a dielectric in the shape of a ball, that the high voltage is generated in the handle of a housing, in order then to be conducted to the electrode by means of a line routed in the housing. With the handle of the housing, the ball-shaped electrode arrangement can be moved over the surface to be treated, for example a skin surface, in such a way as to cover the surface.

SUMMARY

The object of the present invention is to make the delivery of the high voltage to an electrode of the electrode arrangement simpler and more reliable.

In order to achieve this object, according to the invention a planar flexible application piece of the type mentioned in the introduction is characterized in that the application piece comprises a high-voltage stage for generating a high voltage, the output of which is connected to the at least one electrode by a connecting piece on the application piece.

The application piece according to the invention therefore contains not only the electrode arrangement but also the high-voltage stage. This has the advantage that the output of the high-voltage stage can be connected on the shortest path to the at least one electrode of the electrode arrangement. This may be done by means of a correspondingly insulated connecting piece; in a particularly preferred embodiment, the connecting piece is contained as a conductive section inside the dielectric layer. Accordingly, the connecting piece carrying the high voltage may preferably be enclosed by the dielectric enclosing and insulating the at least one electrode, and therefore be insulated reliably against touching. In the application piece according to the invention, the problem of high-voltage delivery over a relatively long distance therefore does not arise. The short conductive section between the high-voltage stage and the at least one electrode of the electrode arrangement may comprise its own insulation, although it is preferably enclosed by the dielectric which also encloses the at least one electrode. To this end, the connecting piece may be a conductor track introduced into the dielectric layer. The conductor track may be arranged as a prefabricated component for connecting the high-voltage stage and the at least one electrode, and then be enclosed by the dielectric, preferably by the injection-molding method. It is, however, also possible to form the conductive section that constitutes the connecting piece inside the dielectric layer from an injection-molded plastic material having conductive additives. In this case, it is expedient to carry out three-stage injection molding, with which a lower level of the dielectric layer, then the conductive layer of the connecting piece, and subsequently the upper level of the dielectric layer is injected. With the production of the conductive section, at the same time the at least one electrode may likewise be produced from a plastic material having conductive additives, and preferably in the same injection-molding step as the connecting piece.

In one embodiment of the invention, the planar flexible application piece may be configured without terminals leading out, if it furthermore comprises batteries for a DC voltage supply and a control circuit for converting the DC voltage into AC voltage signals of a higher peak voltage. The AC voltage signals formed in this way may then be passed to the high-voltage stage. The batteries may likewise be embedded in the dielectric, so that the connecting lines between the batteries and the control circuit, and between the control circuit and the high-voltage stage, can be produced in the same way as the conductive section of the connecting piece. The batteries and parts of the control circuit, in particular a microprocessor chip, may suitably be introduced into the dielectric, in particular when the dielectric is formed by the injection-molding method. In the embodiment with batteries being used, the planar flexible application piece is independent of any voltage supply. The very economically producible batteries, control circuit and high-voltage stage make it possible to configure the planar flexible application piece as a disposable article, which is advantageous in particular for use as a wound dressing because any reconditioning outlay can be obviated. Optionally, the batteries may be made removable from the material of the dielectric, in order to be able to dispose of the batteries separately or to recycle them. The batteries may be conventional disposable batteries, but also rechargeable (accumulators).

In an intermediate stage, the planar flexible application piece comprises only terminals for an AC supply voltage from which the high-voltage stage then generates the required high voltage. In this case, disposal of the batteries is obviated and the connection of the AC voltage supply may be configured in conventional technology because the handling of a high voltage is obviated.

In one embodiment of the invention, an AC voltage passes to the input of the high-voltage stage. The high-voltage stage may generate therefrom AC voltage pulses which have a frequency of between 100 Hz and 100 MHz and are preferably configured as narrow needle pulses with rapidly decaying AC voltage oscillations. The high voltages used lie expediently between 1 kV and 100 kV.

In one embodiment of the invention, the electrode arrangement comprises at least two electrodes, which can be supplied in a phase-shifted manner with the AC high voltage. When AC voltage pulses are used, it may be expedient to deliver the AC voltage pulses in phase opposition to the at least two electrodes, so that a doubled voltage is formed between the electrodes. In this way, the efficiency of the plasma formation in relation to the surface to be treated, in particular the skin surface, can be improved even when the surface to be treated is used as a back electrode, which is for instance at ground potential. In the case of pulses in phase opposition, the ground potential is a zero potential which lies centrally between the two peak voltages of the pulses in phase opposition. This central potential occurs even when the surface, i.e. for example the human or animal body to be treated, is not separately placed at ground potential/earth potential.

The planar flexible application piece according to the present invention may, in one embodiment, be formed as a wound dressing comprising a wound-compatible material. The wound-compatible material may in this case be the material of the dielectric layer. It is, however, also possible to apply a wound-compatible material onto the application surface of the dielectric, which is intended for application on the surface to be treated.

In one simple and preferred embodiment of the invention, the dielectric is configured as an injection-molded part and encloses both the at least one electrode and the high-voltage part on all sides. If a control part and optionally batteries are also provided, these may also be enclosed by the dielectric, so that the dielectric functions as an encapsulation for all the electrical parts of the application piece.

DESCRIPTION OF THE DRAWINGS

In the appended drawings, several exemplary embodiments are described in order to explain the invention. In the drawings:

FIG. 6 shows a sixth embodiment of a planar flexible application piece in a plan view and a sectional representation, FIG. 7 shows a seventh embodiment of a planar flexible application piece in a plan view and a sectional representation.

DESCRIPTION

Figure 1:
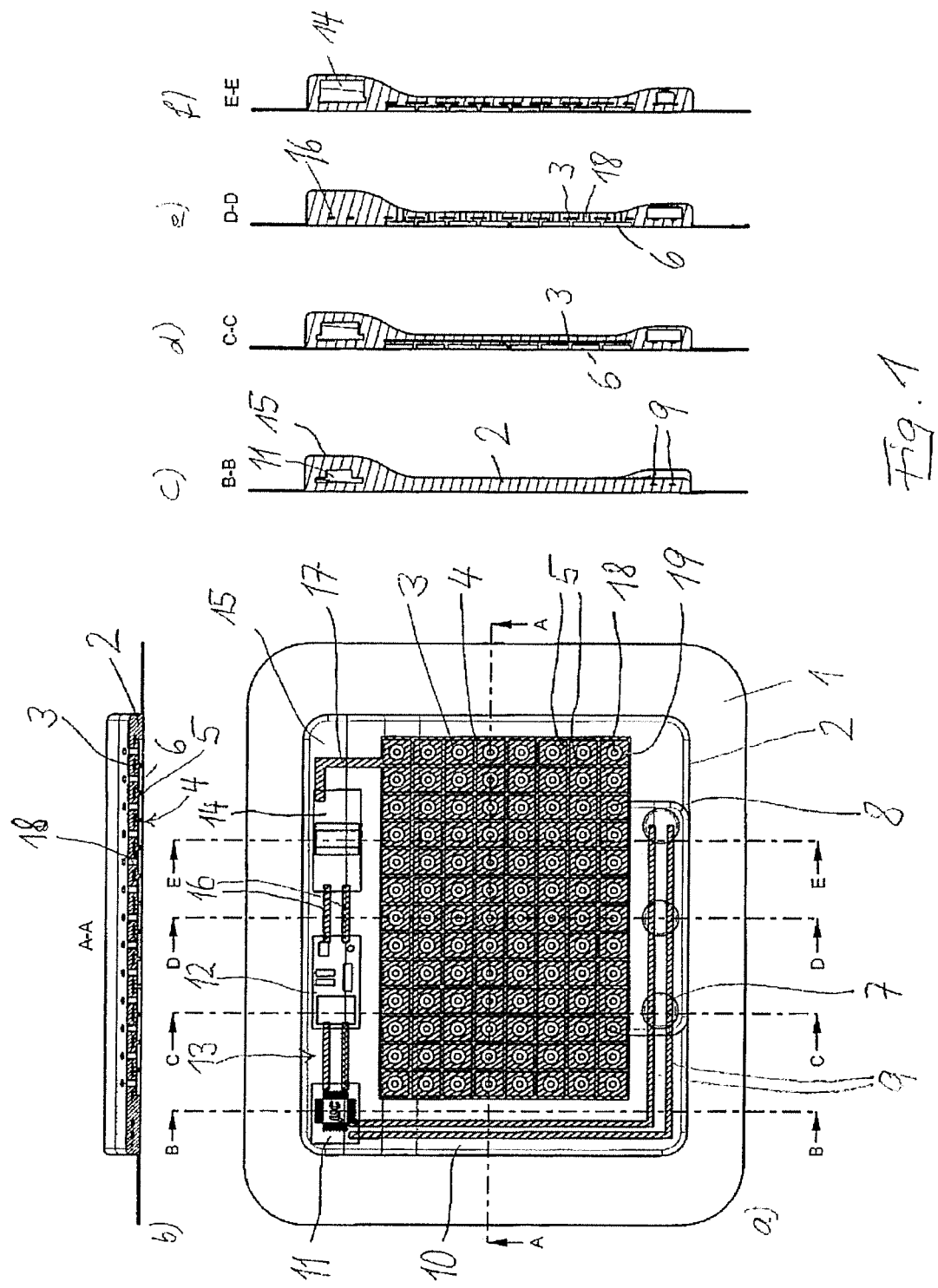
FIG. 1 shows a first embodiment of a planar flexible application piece in a plan view and a plurality of sectional representations.

The exemplary embodiment represented in FIG. 1 is represented in FIG. 1a) in a view from below, with parts inside the application piece, which are not visible during use, being represented. The exemplary embodiment is furthermore represented with the aid of a longitudinal section A-A in FIG. 1a) and a plurality of cross sections B-B (FIG. 1c)), C-C (FIG. 1d)), D-D (FIG. 1e)) and E-E (FIG. 1f).

The application piece represented has an essentially rectangular base shape, in which an edge 1 extends around. The edge 1 may be configured to be pressure-sensitively adhesive on its lower side, in order to be able to adhesively fasten the application piece on the skin of a body part, for example. The circumferential edge 1 may be connected integrally to a dielectric layer 2, which is configured with a larger thickness than the circumferential edge 1. A layer of conductive material as electrode 3 is embedded in the dielectric layer 2, i.e. enclosed on all sides by the material of the dielectric layer 2. In the exemplary embodiment represented, the electrode 3 likewise has a rectangular shape, although on all sides this does not extend as far as the dielectric layer 2, so that the dielectric layer 2 protrudes with edge sections beyond the electrode 3 on every side. It is clear that the represented basic shape of the application piece may also be configured differently, for example polygonally, roundly, ovally or the like. In the region of the electrode 3, the dielectric layer 2 is configured on its lower side in a grid structure 4 which consists of narrow intersecting webs 5, so that in cross section approximately square, downwardly open chambers 6 are formed. Despite their small wall thickness, the webs 5 form a stable grid structure 4, which acts as a spacer when the application piece is applied on a surface to be treated. In this way, in the gas space (air space) of the chambers 6, a stable dielectric barrier plasma discharge caused by the electrode 3 can be formed, with which the treatment of the surface is carried out. The structural stability existing because of the grid structure 4 makes it possible to keep the width of the webs very small, so that the air space in the chambers 6 is optimally large. The width of the webs is, for example, less than ⅕ of the extent of the chambers 6 as measured perpendicularly to the webs.

It is clear to the person skilled in the art that the chambers 6, which are formed in FIG. 1 by webs 5 extending perpendicularly to one another, may also have different shapes, for example rhombic shapes, hexagonal shapes (honeycomb structure), etc. In order that the advantage of the stability of the grid structure 4 is achieved, it is expedient to provide at least four, in particular at least six, and more particularly eight chambers 6 successively in each direction of the dielectric layer 2. For the case in which an elongate electrode arrangement consisting of dielectric layer 2 and electrode 3 is required, it is conceivable to also arrange a smaller number of chambers 6 next to one another in the width direction, if a larger number of chambers 6 is provided in the longitudinal direction. The number of chambers 6 on the lower side of the dielectric layer 2 is in conventional applications at least 12, in particular at least 20, and in many cases at least 40. The exemplary embodiment represented in FIG. 1 comprises thirteen chambers 6 in the longitudinal direction and eight chambers 6 in the width direction, which gives a total number of 104 chambers 6.

In the embodiment represented in FIG. 1, the application piece does not have any terminals leading out, and is thus independently capable of generating a plasma field in the chambers 6 when the surface to be treated, on which the application piece is then applied, functions as a back electrode. The application piece therefore comprises a single electrode 3, which must be supplied with a high voltage in order to generate a plasma field in the chambers 6.

For supplying the electrode 3, three batteries 7, here in the form of button cells, are provided in the application piece.

The batteries are located in a lower edge piece 8 of the dielectric layer 2, which edge piece may be configured to be thickened in a bulging manner in order to receive the batteries, as can be seen in the sectional representations C-C and D-D (FIGS. 1*d*) and *e*)). The batteries 7 are connected to one another by conductor tracks 9 embedded in the dielectric layer 2. The conductor tracks 9 extend over a lateral edge piece 10 of the dielectric layer as far as a microcontroller chip 11. Together with an electronic signal shaper 12, the microcontroller 11 forms a control apparatus 13. The output of the control apparatus 13, formed by the output of the signal shaper 12, is connected to the input of a transformer stage 14 which is used to form a working high voltage of, for example, 15 kV from an input voltage of, for example, 250 V. The arrangement consisting of control apparatus 13 and transformer stage 14 is located in an upper edge piece 15 of the dielectric layer 2.

As illustrated by the sectional representations of FIGS. 1*c* to 1*f*, the upper edge section 15 is likewise configured to be thickened relative to the dielectric layer 2 in the region of the electrode 3 in order to receive the electronic components. The electrode 3 does not extend into the edge pieces 8, 10 and 13.

The microcontroller chip 11, the signal shaper 12 and the transformer stage 14 are connected to one another by conductor tracks 16 embedded in the dielectric layer 2, which are configured in the same way as the conductor tracks 9.

The connection of the output of the transformer stage 14 to the electrode 3 takes place by means of a high-voltage conductor track 17 suitable for transferring a high voltage, said high-voltage conductor track being able to be formed as a single appendage of the electrode 3.

The microcontroller chip 11 receives its supply voltage from the batteries 7, which may be electrically connected in series in order to provide the summed cell voltages as a supply voltage of the microcontroller chip 11. The microcontroller chip 11 controls the formation of AC voltage pulses in the signal shaper 12, which are stepped up from the supply voltage of the batteries, of a few V, to an AC voltage with a peak voltage of about 250 V. This AC voltage is passed to the transformer stage 14 in order to form high-voltage pulses, for example by means of discharge paths (not represented), in which case the high-voltage pulses (with alternating polarity) may represent AC voltage trains with a rapidly decreasing amplitude because of a certain tuned circuit behavior. By means of the high-voltage pulses, the electrode 3 is brought alternately to a high positive and negative potential relative to the surface to be treated, which acts as a back electrode, so that the desired dielectric barrier plasma discharge can take place in the gas (in particular air) contained in the chambers 6.

FIG. 1 also shows that the dielectric layer 2 delimiting the chambers 6 upward is provided with through-openings 18 through which, for example, fluid may be aspirated from the surface before, during or after the plasma treatment, or as an alternative a treatment gas can be fed into the chambers 6 before or during the treatment.

In order to shield the electrode 3 with the dielectric layer 2 in the region of the through-opening, for each through-opening 18 the electrode 3 comprises a recess 19 which is larger than the through-opening 18, so that the wall of the through-opening 18 is formed without interruption by the material of the dielectric layer 2.

Even though each chamber is provided with a through-opening 18 in the exemplary embodiment represented, this does not mean that such a configuration is necessary. Aspiration of fluid may also be carried out through a much smaller number of through-openings 18. This applies in particular when the webs 5 of the grid structure 4 allow—at least partially—fluid communication between the chambers 6. In the exemplary embodiment represented, each chamber 6 is provided with a through-opening 18. This makes it possible to form webs 5 with a constant height, so that the webs 5 form substantially closed chambers 6 when the application piece is applied on the surface to be treated. In the case of unevenly configured surfaces, this is also achieved in that both the material of the dielectric layer 2 and the material of the electrode 3 are flexible, so that the application piece can adapt to an uneven surface, for example a skin surface or wound surface.

Figure 2:
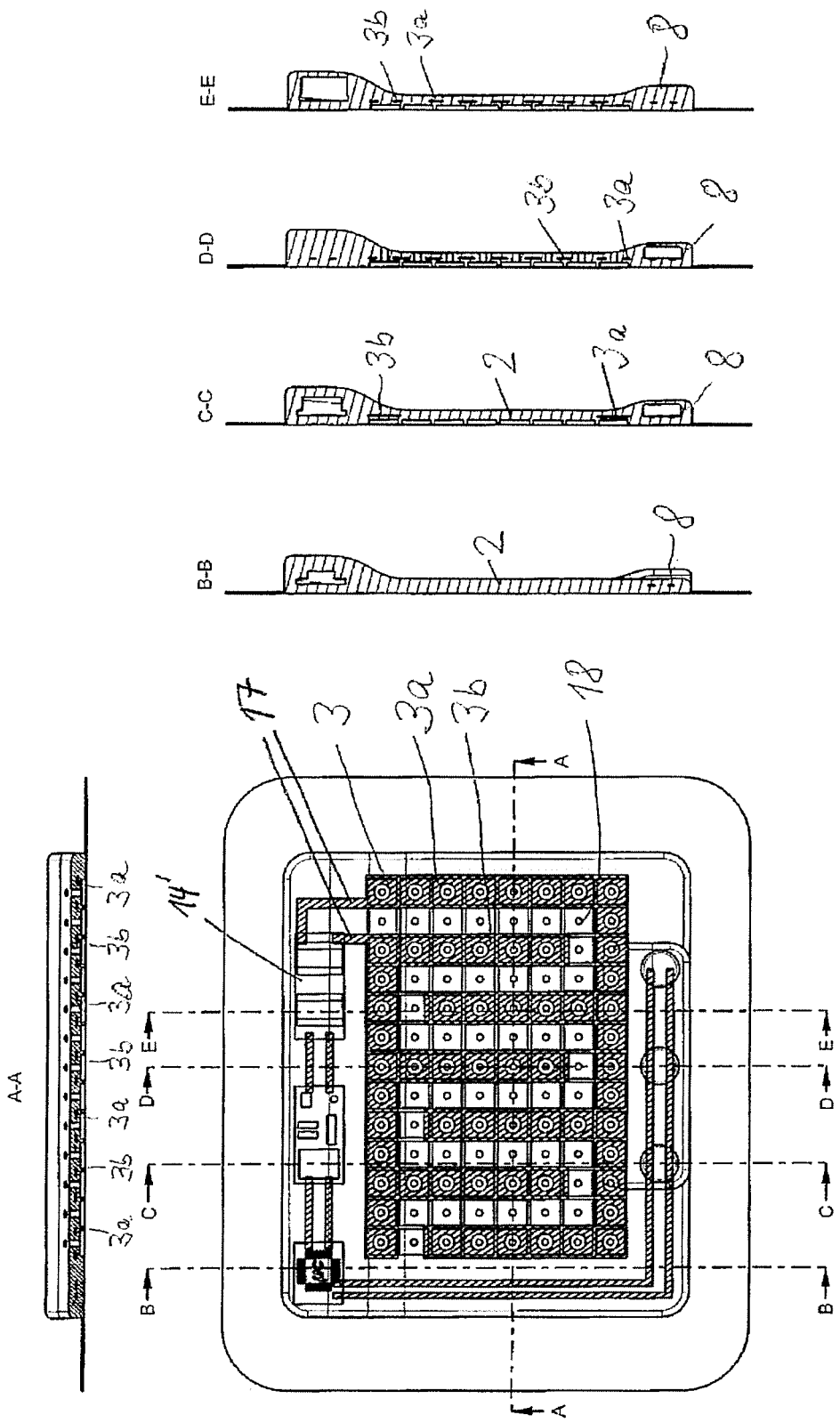
FIG. 2 shows a second embodiment of the planar flexible application piece in a plan view and a plurality of sectional representations.

The second embodiment, represented in FIG. 2, differs from the embodiment of FIG. 1 only in that the electrode 3 is formed by two partial electrodes 3*a*, 3*b*, which are configured to engage in one another in the manner of a comb. Between the partial electrodes 3*a*, 3*b*, there is an insulating strip configured in a meandering shape through the material of the dielectric layer, because there is no electrically conductive electrode layer in this region. FIG. 2 illustrates that this configuration of the electrode 3 does not alter the rest of the construction of the application piece. In particular, the chambers 6 may be present both in the region of the partial electrodes 3*a*, 3*b* and in the region of the insulating strip. Likewise, in this case as well the through-openings 18 are provided for each chamber 6.

The partial electrode 3*a* and 3*b* are supplied by the transformer stage 14', in a manner which is as in-phase as possible, with high-voltage pulses of mutually reversed polarity. This gives rise to a plasma field between the partial electrodes 3*a*, 3*b* relative to the back electrodes formed by the surface, but also a voltage difference that is two times as great between the two partial electrodes 3*a*, 3*b*, so that the plasma formation by the electric field present between the partial electrodes 3*a* and 3*b* is improved further.

The transformer stage 14' is in this case provided with two transformer coils, which are poled oppositely to one another and thus respectively supply one of the two partial electrodes 3*a*, 3*b* with the voltage pulses. Correspondingly, there is also respectively a high-voltage conductor track 17 between the transformer stage 14' and the partial electrodes 3*a* and 3*b*.

Figure 3:
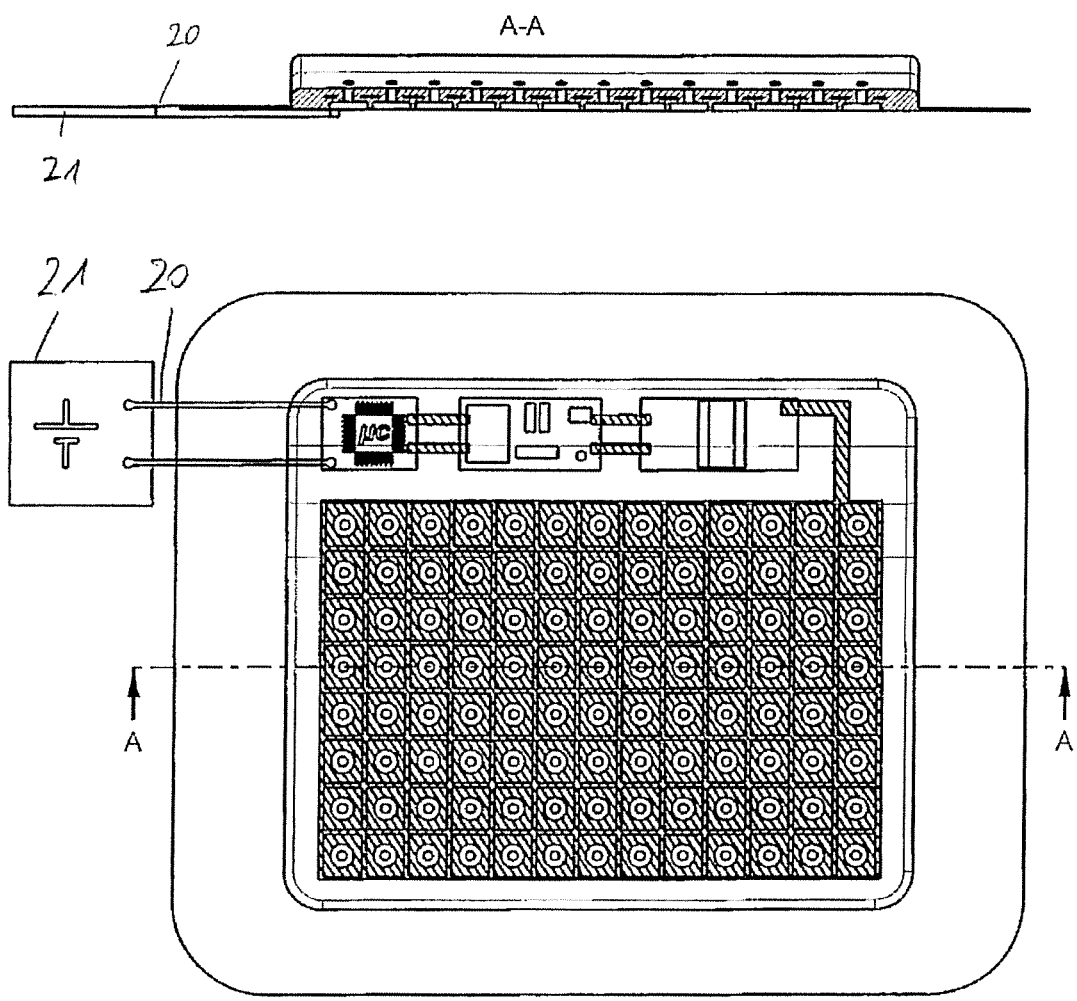
FIG. 3 shows a third embodiment of a planar flexible application piece in a plan view and a sectional representation.

The exemplary embodiment represented in FIG. 3 corresponds to the exemplary embodiment according to FIG. 1, with the difference that independent batteries 7 are not provided. Rather, in this exemplary embodiment the application piece is provided with terminals 20 leading out to which a DC voltage source 21 can be connected. The terminals 20 may in this case be located on an appendage of the application piece, and correspondingly contacted, or else formed by a connecting cable with which the connection to the DC voltage source 21 is established. The DC voltage source 21 replaces only the batteries 7, so that the construction and the function of the application piece remain unchanged. Since batteries 7 do not have to be contained in the application piece, the lower edge piece 8 of the exemplary embodiment according to FIG. 1 may be omitted.

Figure 4:
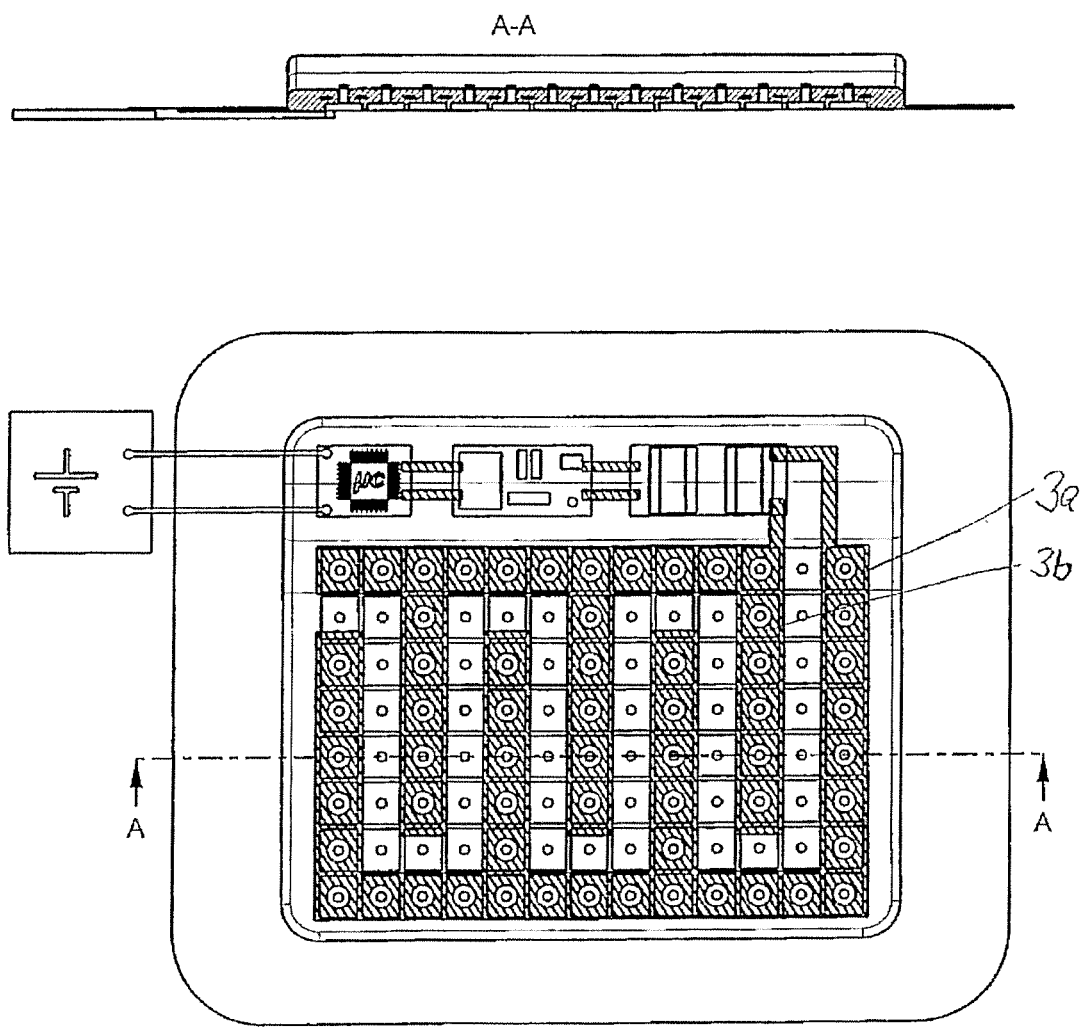
FIG. 4 shows a fourth embodiment of a planar flexible application piece in a plan view and a sectional representation.

The exemplary embodiment represented in FIG. 4 is identical to the exemplary embodiment according to 3, but concerns an application piece having two partial electrodes 3*a*, 3*b*, while the exemplary embodiment according to FIG. 3 relates to a single electrode 3. In this regard as well, the functions are the same as described with respect to FIGS. 1 and 2.

Figure 5:
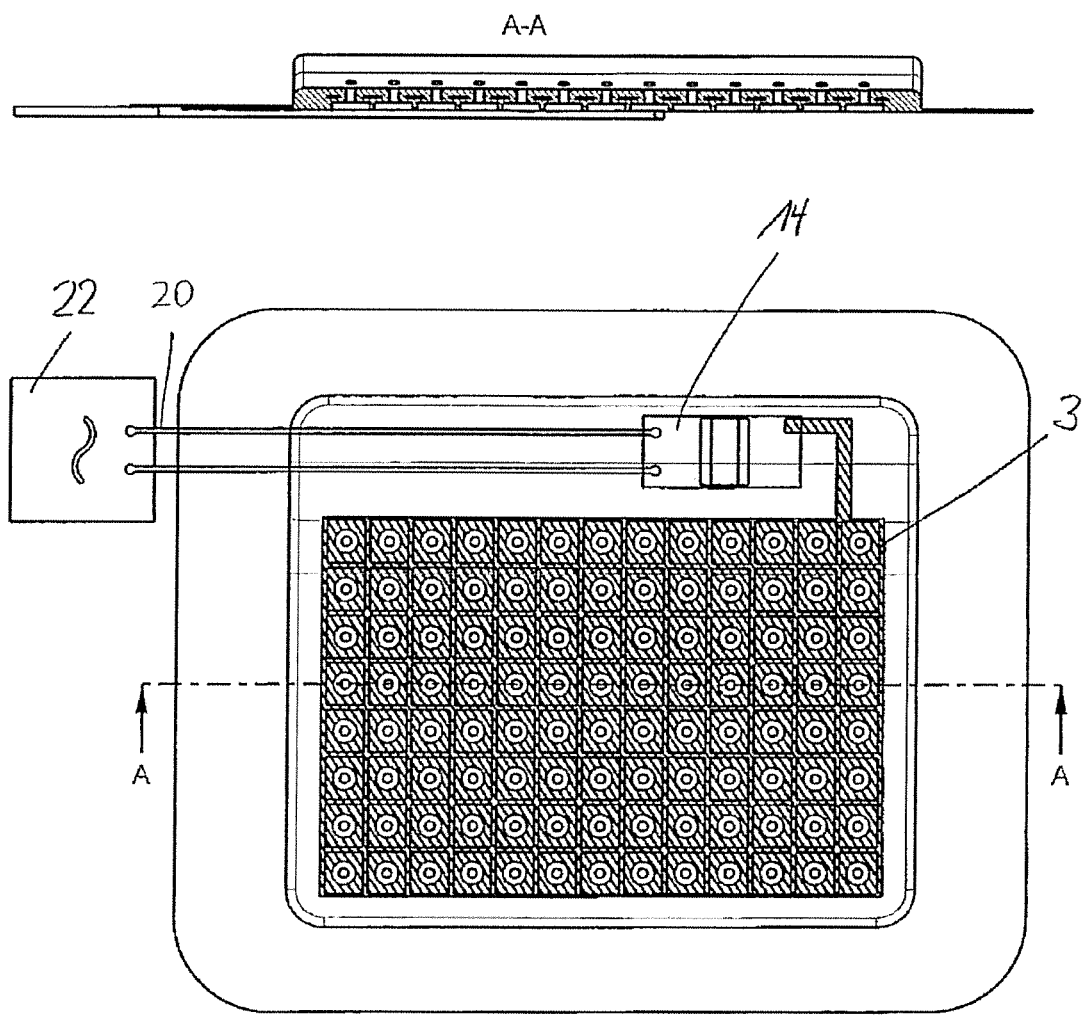
FIG. 5 shows a fifth embodiment of a planar flexible application piece in a plan view and a sectional representation.

The fifth embodiment, according to FIG. 5, only still contains the transformer stage 14 on the application piece. In this embodiment as well, the application piece contains terminals 20 for connecting to an external voltage supply apparatus, which is formed here by an AC voltage supply 22, from which the transformer stage 14 generates the suitable high-voltage pulses for the formation of a plasma between the electrode 3 and the surface to be treated.

According to FIG. 6, the connection of an AC voltage supply directly to a transformer stage 14 may also be used for an appendage piece having two partial electrodes 3a, ab—as described above. In the embodiments according to FIGS. 5 and 6, the AC voltage supply and the signal shaping are carried out externally. The advantage nevertheless remains that high-voltage signals, which are critical in terms of safety technology, do not need to be transmitted onto the appendage piece since the high-voltage signals are only generated in the transformer stage 14 inside the appendage piece and are conducted on a short path, for example with the embedded high-voltage conductor tracks 17, to the electrode 3, or to the partial electrodes 3a, 3b. As described, the high-voltage conductor tracks 17 may be embedded in the dielectric layer, so that the insulation of the high-voltage lines 17 inside the dielectric layer 2 also takes place with the shielding of the electrode 3, or of the partial electrodes 3a, 3b, with the same technology.

The seventh exemplary embodiment, represented in FIG. 7, corresponds to the first exemplary embodiment according to FIG. 1, although in this case the batteries 7, the conductor tracks 9, 16, the microcontroller chip 11, the signal shaper 12 and the transformer stage 14 are not enclosed by the material of the dielectric layer 2 but are mounted on the material of the dielectric layer 2, as illustrated in particular by FIG. 7b. The conductor tracks 9, 16 may in this case be applied directly onto the dielectric layer 2, or printed onto a film which is in turn adhesively bonded onto the dielectric layer 2. The electrical part is covered by a housing 23, which is applied onto the dielectric layer and forms a downwardly open channel extending around in the shape of a strip on the edge of the dielectric layer 2, which channel is closed underneath by the dielectric layer 2. The housing 23 consists of an insulating material and, in order to obtain the flexibility required for adaptation of the application piece to uneven surfaces, may consist of an insulating, geometrically stable but pliable material, for example an elastomer.

The formation of an annularly closed housing 23 leads to versatile usability of the application piece, without creating a preferential direction. It is, however, also possible to configure the housing in the form of a strip only on one edge or—depending on requirements—with an L-shape or U-shape.

FIG. 7c) illustrates that the supply of the high voltage to the electrode 3 is carried out with a high-voltage conductor track 17, which extends above the dielectric layer 2 and, through an opening of the dielectric layer 2, contacts an appendage, routed in the dielectric layer 2, of the electrode 3 with a projection 17'. In this case as well, the high voltage is led only over a short distance and can be readily protected by the housing 23 against touching and sparking.

In all the exemplary embodiments, the dielectric layer 2 may preferably be produced by initially casting a lower level of the dielectric layer 2, on which the electrode 3 is placed, whereupon an upper level of the dielectric layer is then cast, which is integrally connected to the lower level. As an alternative thereto, a lower level of the dielectric layer may be prefabricated, the electrode 3 then put in place, and finally an upper level of the dielectric layer 2 applied in prefabricated form. The two layers may then be adhesively bonded, or preferably welded using reflectors, to one another in an insulating manner. In yet another embodiment, the dielectric layer 2 may be produced integrally in one step by injection molding, the electrode 3 being placed in the injection mold.

In a similar way, the electrical components, such as batteries 7, microcontroller chip 11, signal shaper 12 and transformer stage 14, may be integrated with the conductor tracks 9, 16 and 17 into the dielectric layer. The thickening of the dielectric layer 2 in the lower edge piece 8 and in the upper edge piece 15 may, for example, be carried out during manufacture of the upper level of the dielectric layer 2 by the injection-molding method.

In all the embodiments represented, the application piece according to the invention may be configured and used as a disposable article. In the embodiments of FIGS. 1, 2 and 7, the entire arrangement is disposed of, and in the other embodiments the connection to an external apparatus is merely released. In the case of connecting the application piece to a reduced-pressure source for the purpose of aspirating wound secretion, a material that absorbs the aspirated liquid may be arranged on the upper side of the dielectric layer, for example under an airtight film which assists the aspiration.

The application piece according to the invention is suitable, in particular, as a wound dressing which can remain on the wound for the entire duration of the healing of the wound, because the dielectric barrier plasma treatment can be initiated periodically for a required treatment time by the microcontroller chip 11, with the result that the entire wound region can be repeatedly made germ-free so that accelerated healing of the wound is achieved. This is contributed to by a continuous increase, resulting from the plasma discharge, of the microcirculation in and around the wound region and/or in and around the intact skin.

The invention claimed is:

1. A planar flexible application piece, comprising:
   an electrode arrangement, which can be supplied with a high voltage, for a dielectric barrier plasma treatment of a surface to be treated, the electrode arrangement comprising at least one planar electrode and a dielectric layer of a planar flexible material having a bearing face for the surface to be treated, said dielectric layer electrically shielding the at least one electrode from the surface to be treated in such a way that only a dielectric barrier current can flow between the at least one electrode and the surface to be treated when a plasma field is formed in a gas space between the electrode arrangement and the surface to be treated by a high voltage of the at least one electrode;
   a high-voltage stage for generating the high voltage wherein the high-voltage stage is contained inside the dielectric layer; and
   a connecting piece, wherein an output of the high-voltage stage is connected to the at least one electrode by the connecting piece, wherein the connecting piece is contained as a conductive section inside the dielectric layer.

2. The application piece as claimed in claim 1 wherein the connecting piece is a high-voltage conductor track inside the dielectric layer.

3. The application piece as claimed in claim 2 wherein the high-voltage conductor track comprises an injection-molded plastic material having conductive additives.

4. The application piece as claimed in claim 2 wherein the high-voltage conductor track is a metallic conductor track.

5. The application piece as claimed in claim 1 further comprising terminals for an AC voltage supply which passes to the high-voltage stage.

6. The application piece as claimed in claim 1 further comprising batteries for a DC voltage supply and a control circuit for converting the DC voltage into AC voltage signals of a higher peak voltage, wherein the AC voltage signals pass to the high-voltage stage.

7. The application piece as claimed in claim 1 wherein the high voltage is an AC voltage the electrode arrangement comprises at least two partial electrodes which can be supplied in a phase-shifted manner with the high voltage.

8. The application piece as claimed in claim 1 wherein the application piece is formed as a wound dressing comprising a wound-compatible material.

9. The application piece as claimed in claim 8 wherein the wound-compatible material is configured to be applied onto the bearing face of the dielectric.

10. The application piece as claimed in claim 1 wherein the dielectric layer is configured as an injection-molded part and encloses both the at least one electrode and the high-voltage stage on all sides.

\* \* \* \* \*